(12) United States Patent
Shvartsberg et al.

(10) Patent No.: US 8,513,946 B2
(45) Date of Patent: Aug. 20, 2013

(54) MOVABLE TABLE FOR MAGNETIC RESONANCE IMAGING

(75) Inventors: Alexander Shvartsberg, Winnipeg (CA); Labros Petropoulos, Chgrin Falls, OH (US)

(73) Assignee: Imris Inc., Winnipeg, MB (CA)

( * ) Notice: Subject to any disclaimer, the term of this patent is extended or adjusted under 35 U.S.C. 154(b) by 556 days.

(21) Appl. No.: 12/780,085

(22) Filed: May 14, 2010

(65) Prior Publication Data

US 2010/0327870 A1    Dec. 30, 2010

Related U.S. Application Data

(60) Provisional application No. 61/221,281, filed on Jun. 29, 2009.

(51) Int. Cl.
  *G01V 3/00*    (2006.01)
(52) U.S. Cl.
  USPC ............................ 324/318; 324/319; 600/410
(58) Field of Classification Search
  USPC ................. 324/318, 319, 322; 600/410, 415
  See application file for complete search history.

(56) References Cited

U.S. PATENT DOCUMENTS

| | | | |
|---|---|---|---|
| 4,771,785 A * | 9/1988 | Duer ............................ | 600/415 |
| 5,525,905 A * | 6/1996 | Mohapatra et al. ............ | 324/318 |
| 5,735,278 A | 4/1998 | Hoult et al. | |
| 6,045,262 A | 4/2000 | Igeta | |
| 6,246,239 B1 * | 6/2001 | Krogmann et al. ............ | 324/318 |
| 6,459,923 B1 * | 10/2002 | Plewes et al. ................. | 600/411 |
| 6,822,447 B1 | 11/2004 | Yamagata | |
| 7,319,325 B2 | 1/2008 | Petot et al. | |
| 7,446,304 B2 | 11/2008 | Li | |
| 7,486,076 B2 | 2/2009 | Nagao | |
| 2005/0154291 A1 | 7/2005 | Zhao et al. | |
| 2009/0306494 A1 | 12/2009 | Scarth et al. | |
| 2009/0306495 A1 | 12/2009 | Scarth et al. | |

* cited by examiner

*Primary Examiner* — Louis Arana

(74) *Attorney, Agent, or Firm* — Adrian D. Battison; Ade & Company Inc.

(57) ABSTRACT

In MR imaging, the patient is placed on the table in a configuration convenient for a surgical procedure and while in the configuration the patient is moved into the field of view by moving the magnet longitudinally and the table is moved in the bore relative to the magnet so as to optimize the part to be imaged within the field of view of the magnet. After imaging the table is moved back to the preset position and removed from the magnet for the surgical procedure to commence or continue. The movement includes movement along the longitudinal axis; transverse movement side to side; rolling movement about a longitudinal axis; tilting movement about a transverse axis and bending movement of the table relative to at least one transverse hinge line in the table at a position spaced from the ends of the table.

23 Claims, 6 Drawing Sheets

MOVABLE TABLE FOR MAGNETIC RESONANCE IMAGING

This application claims the benefit under 35 U.S.C.119 of Provisional Application Ser. No. 61/221,281 filed Jun. 29, 2009.

This invention relates to a patient support table for use in magnetic resonance imaging and to a method for using the table.

BACKGROUND OF THE INVENTION

With MRI, a high field magnet, typically superconducting, is arranged in a torus configuration and with the patient lying down inside the magnet on a table where the magnetic field allows a pulsed and sequenced magnetic and EM field to probe the body to produce images, which allow the trained radiologist to determine with high probability the anatomy of the patient. MRI techniques are very good at detecting the anatomical location of different diseases, for example, tumours.

The magnet for highest field strength is generally cylindrical with the patient lying along the bore but other magnet shapes and arrangements are used in lower strength configurations.

Most MR imaging is carried out on a diagnostic basis where the patient is placed on a diagnostic table which moves into the bore and carries the patient to a required position. In these cases the patient is normally conscious and thus can be moved to the required location on the table so that, when the table enters the bore, the part of the patient to be imaged is located relative to the table so that it enters the bore at the field of view of the MR system, generally at the center of the bore on the axis. In most cases therefore the table is movable only longitudinally of the bore to move the patient into and out of the bore.

The table also is prevented from any significant movement relative to the bore since it includes mechanical structures which fill the available part cylindrical area underneath the surface of the table.

In U.S. Pat. No. 5,735,278 (Hoult et al) issued Apr. 7, 1998, disclosed a medical procedure where a magnet is movable longitudinally relative to the table and to the patient on the table. The moving magnet system allows intra-operative MRI imaging to occur more easily in neurosurgery patients, and has additional applications for liver, breast, spine and cardiac surgery patients. The table is set up for the required surgery and the magnet is moved into place over the table to effect the imaging. The table can tilt about a transverse axis and rotate about a longitudinal axis.

Related disclosures are made in U.S. application Ser. No. 12/333,032 filed Dec. 11, 2008 and Ser. No. 12/420,859 filed Apr. 8, 2009 by the present Assignees, the disclosures of which are incorporated herein by reference, which correspond to PCT Applications CA/2009/000672 and CA/2009/00673 filed May 25 2009, to which reference may be made for further detail.

U.S. Pat. No. 7,319,325 (Petot) issued Jan. 15, 2008 and assigned to Philips claims the use of a position sensor to provide feed back to the drive system of a table within the bore of an MRI magnet. The movement as disclosed appears to be simply linear movement along the bore.

U.S. Pat. No. 7,486,076 (Nagao) issued Feb. 3, 2009 and assigned to Ricoh or Hitachi discloses moving the table based on information relating to the difference between the actual position and a desired position. Movement in a second direction at right angles to the longitudinal direction is possible during whole body scanning.

U.S. Pat. No. 6,822,447 (Yamagata) issued Nov. 23, 2004 and assigned to Toshiba discloses moving the table in two directions to move the point of interest to the required imaging position in the magnet.

U.S. Pat. No. 6,045,262 (Igeta) issued Apr. 4, 2000 and assigned to Hitachi discloses a table which is used in X-ray and MRI which can be moved in two directions.

Published US Patent Application 2005/0154291 (Zhao) published Jul. 14, 2005 discloses a table which is used in MRI which can be moved in two directions and tilted during imaging in the magnet.

SUMMARY OF THE INVENTION

It is one object of the present invention to provide a patient support table for use in magnetic resonance imaging.

According to a first aspect of the invention there is provided a method for imaging of a part of a patient using Magnetic Resonance prior to or at one or more intermediate times during a surgical procedure, the method comprising:

using an MRI system including a magnet arrangement having a field of view and a patient support table for supporting a patient;

outside the magnet, placing the patient on the table in a configuration arranged for the surgical procedure;

while the patient remains substantially stationary in the configuration on the table, causing movement of either the table or the magnet so that the patient is moved into the field of view of the magnet;

while the patient remains substantially stationary in the configuration on the table and while the patient is in the field of view, causing movement of the table relative to the magnet so as to adjust the position of the patient relative to the field of view so as to locate the position of the part of the patient to be imaged more effectively within the field of view of the magnet;

while the patient remains substantially stationary in the configuration on the table, causing movement of either the table or the magnet so that the patient is removed from the magnet for the surgical procedure.

In one preferred arrangement the imaging is carried out while the table and the magnet remain stationary.

In another alternative arrangement the table is continuously articulated inside the bore during imaging. This movement can be carried out in any one or more of the available degrees of movement of the table. The movement allows the body part of the patient to be scanned through the imaging zone during the imaging process to provide effective imaging of different locations in the part of the patient to be imaged. This articulation can be coordinated with the control system of the MR imaging suite to provide another control tool for the imaging process together with the traditional systems for control of slice selection and image position.

Preferably the position of the patient is adjusted to optimize the position of the part to be imaged in the field of view.

Preferably the table is returned to a pre-set position prior to removal from the bore.

Preferably in one of the configurations the patient is prone and the table is arranged to tilt the head downwardly and forwardly.

Preferably the table provides a hinge line across the hips of patient allowing a forward part of the table with the upper body of the patient thereon to tilt downwardly and forwardly.

Preferably the table includes a head holder which allows the head of the patient to tilt downwardly from the end of the table.

Preferably the table includes a hinge portion which tilts upwardly and forwardly with the head holder beyond the end of the hinge portion.

Preferably in one of the configurations the patient is arranged for surgery in the groin area and wherein the table is arranged with a first portion on which the upper body part is received, a hinge line in the area of the hips and a second part to receive the lower body part hinged at the hinge line relative to the first part.

Preferably the second part includes an opening through which the groin area can be accessed.

Preferably the opening extends from one side part way across the table.

Preferably in one of the configurations the patient is arranged for surgery of the breast and wherein the table is arranged with an arched portion onto which the patient is placed in prone position, the arched portion having an opening from the sides through which the breast can be accessed.

The table may be designed with a base or pedestal and a plurality of table top portions each designed for use with a respective procedure.

In one arrangement, the table is designed for use in a configuration where the patient is prone. The patient is positioned face down, where cushions or mattresses are utilized to support the areas of the body that are not being operated upon. Retractors or Fixation devices incorporated on the table help to fixate and immobilize various parts of the body like cervical spine, head, lumbar spine, thoracic spine to avoid any movement during surgery. The table can be rotated, tilted, moved axially or horizontally or longitudinally to the correct imaging position for an image to be obtained.

In another arrangement, the configurations are groin surgery. The patient can be positioned face up (supine) or face down (prone) position. For prostate imaging the patient is positioned face up with feet first facing the magnet. The groin area of the patient is elevated for the access to the rectum via endovascular probe that allows real time imaging and tracking of an biopsy device or a brachytherapy device.

In another arrangement, in a configuration for groin surgery the patient is positioned on a side fetal position and follows the procedures as above.

According to a second aspect the invention provides an apparatus for use in imaging of a part of a patient using Magnetic Resonance comprising:

a magnet arrangement having a field of view;

a patient support table for supporting a patient;

a control system for controlling relative movement of the table and the magnet;

the patient support table being arranged for movements which include at least:

longitudinal movement along the longitudinal axis of the table;

transverse movement side to side;

rolling movement about a longitudinal axis of the table;

tilting movement about a transverse axis of the table;

a bending movement of the table relative to a transverse hinge line in the table at a position spaced from the ends of the table;

the control system being arranged to effect said movements while the patient support table is within the field of view.

DETAILED DESCRIPTION

Figure 1:
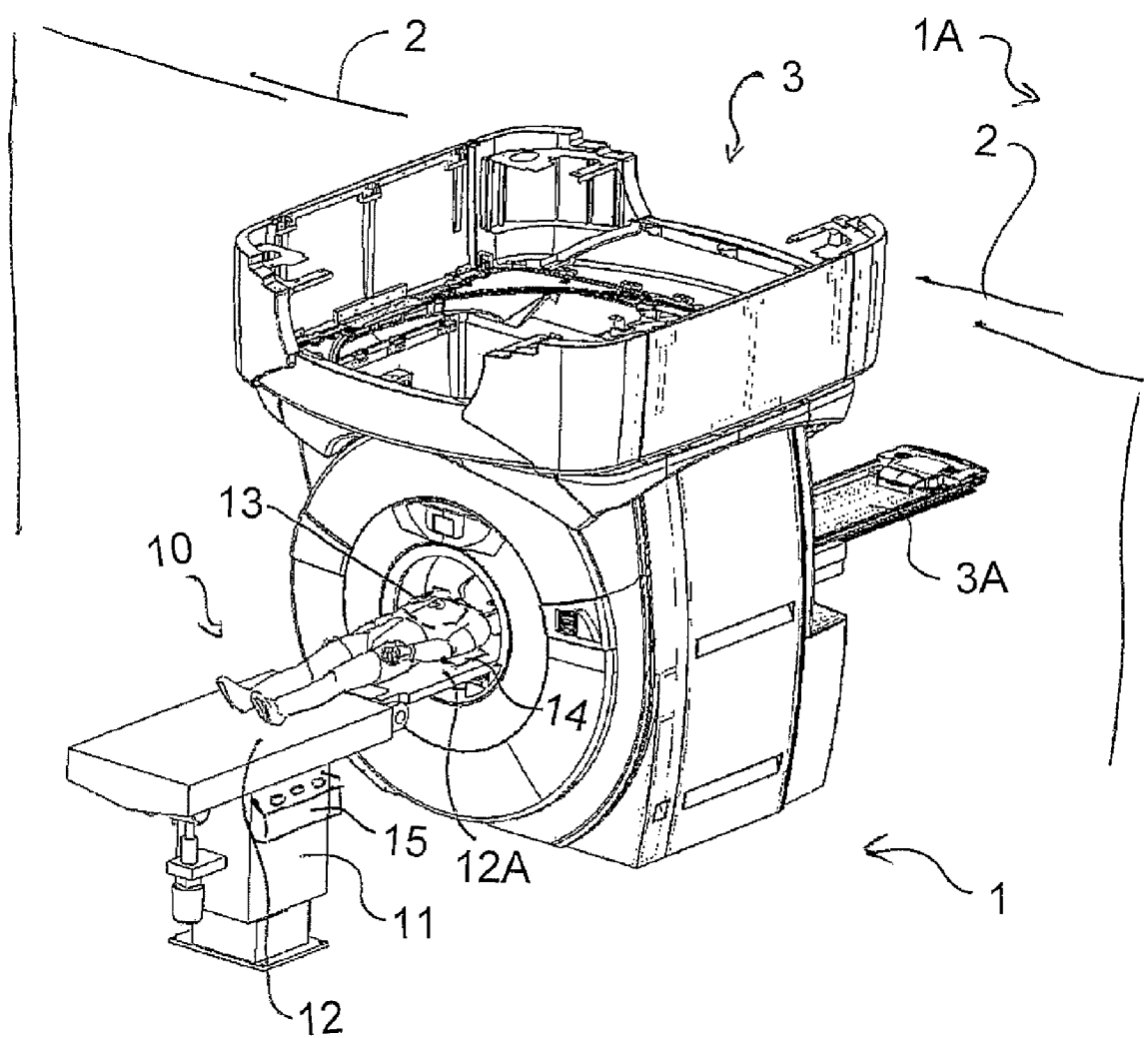
FIG. 1 is an isometric schematic view of an MRI system according to the present invention.

In FIG. 1 is shown an arrangement for carrying out Magnetic Resonance Imaging of a patient while the patient remains stationary on a patient support table. The arrangement provides a room 1 in which is mounted a patient support table 10 with doors 2 at one side of the room for entry into the room of the magnet 3 of an MR imaging system from a magnet bay 1A.

The MR imaging system is a high-field (e.g. 1.5T or 3T) magnet that moves on overhead rails between the two or more rooms.

The Patient Handling System or support table is shown in FIG. 1 is indicated generally at 10. The patient support table includes a base or pedestal 11 which allows the base to move a patient support portion 12 to required locations in height and in orientation. At the top of the base 11 is mounted the patient support portion 12 in the form of a generally planar body 12A formed of a fiber reinforced plastics material so as to define a surface area sufficient for supporting the patient while lying on the patient support portion.

An anterior coil 13 is arranged to be placed on top of the part of the patient to be imaged when in place for imaging on the mattress and also a posterior coil 14 is arranged to be place behind the patient.

The apparatus further includes a control system 15 for controlling relative movement of the table 10 and the magnet 3.

Figure 2:
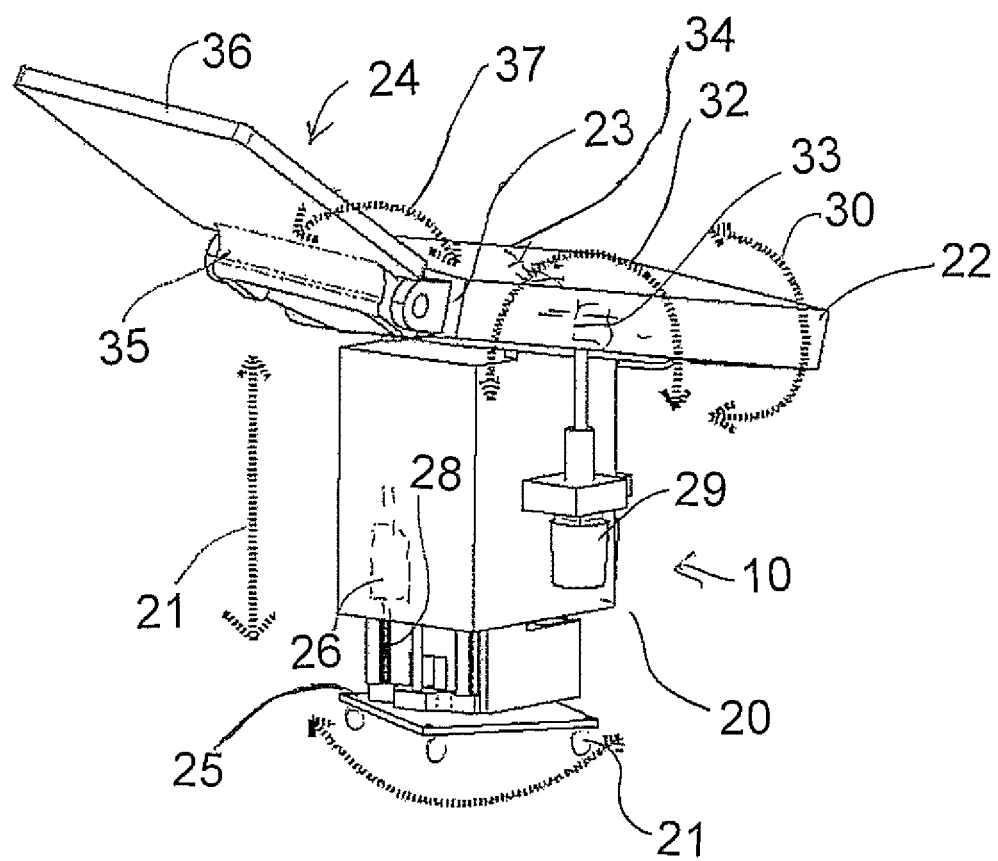
FIG. 2 is an isometric view of the table of FIG. 1.

In FIG. 2 is shown the table itself which is separate from the magnet 3 of FIG. 1 and is arranged for insertion into one end of the cylindrical bore of the magnet 3 generally at the end of the bore opposite to the conventional diagnostic table 3A of the magnet.

The table 10 comprises a pedestal 20 which can be mounted on ground wheels 21 or the ground wheels may be omitted for increased stability. The ground wheels if present can be locked to prevent transverse movement or can be retracted to place the pedestal base firmly on the floor.

The pedestal base carries at its upper end a table member 22 which is in the form of a generally flat table portion defining a first part of the table on which the patient can lie. The table member includes, at its outer or forward end, a coupling 23 to which a table top portion 24 can be mounted. The coupling 23 provides physical connection from the table top portion 24 to the table member 22 so that forces from the patient lying on the table top portion can be transferred into the table member to hold the patient in fixed position. The table top portion is cantilevered outwardly from the forward end of the table member 22. The table top portion 24 is removable from the coupling 23 so that it is replaceable by alternative constructions for example of the type described hereinafter.

The table member 22 is mounted on the pedestal in a manner which provides movement of the table top member 22 relative to the pedestal in a plurality of different directions.

In a first direction of movement, the pedestal 20 can pivot around a vertical axis relative to a base portion 25 so that the whole of the table can swivel about the vertical axis. Typically this swivel movement is effected manually since it is relatively course movement and since there is sufficient mechanical advantage from the structure of the table to allow easy manual movement of the rotation of the table about the vertical axis.

In addition the pedestal includes a first motor 26 in the form of a linear actuator which can drive upward and downward movement 27 of the pedestal relative to the base. The linear actuator can be of the type including a lead screw shown schematically at 28.

A further motor 29 provides tilting movement of the table member in a rolling action as indicated at 30 around a horizontal axis generally longitudinal of the table.

Figure 3:
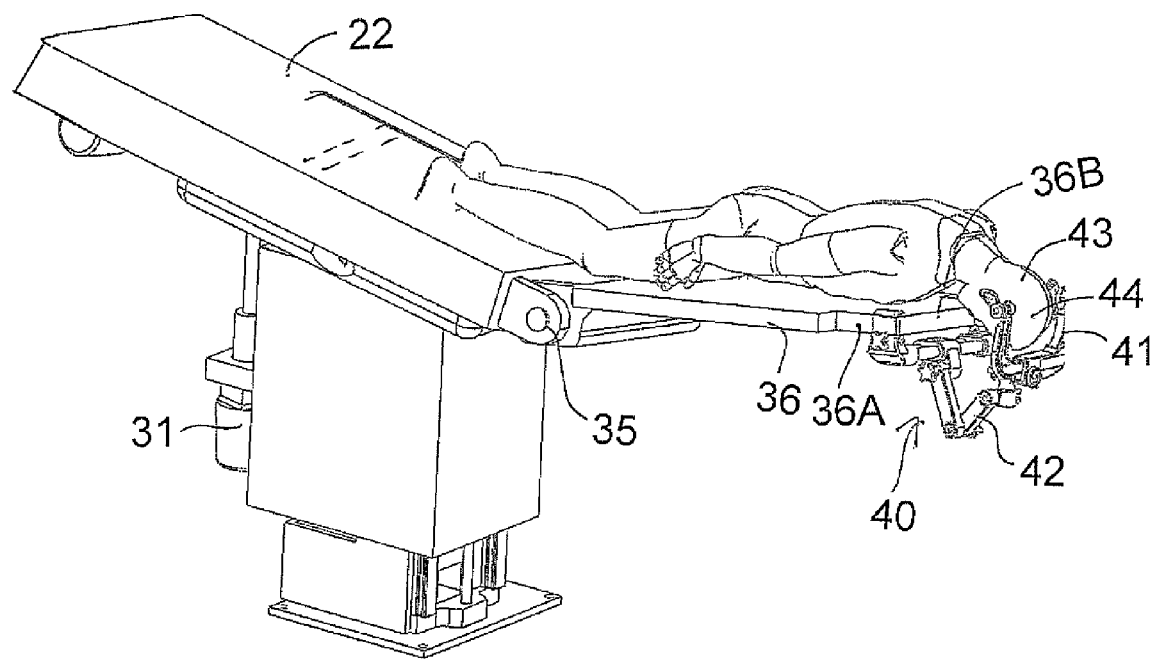
FIG. 3 is an isometric view of the table of FIG. 1 for mounting the patient showing a configuration for a head procedure.

A further motor 31 visible in FIG. 3 provides tilting movement of the table about a transverse axis so as to raise and lower the front end of the table relative to the pedestal and thus tilt the patient about the transverse axis. The tilting movement is shown in FIG. 2 at 32.

Two additional motors are provided as indicated schematically at 33 and 34 which act to provide longitudinal movement of the table forwardly and rearwardly relative to the pedestal and also side to side movement of the table relative to the pedestal.

All four of the above motors are accurate motors providing controlled slow movement of the table top relative to the pedestal so as to ensure accurate positioning of the patient on the table as required.

Figure 5:
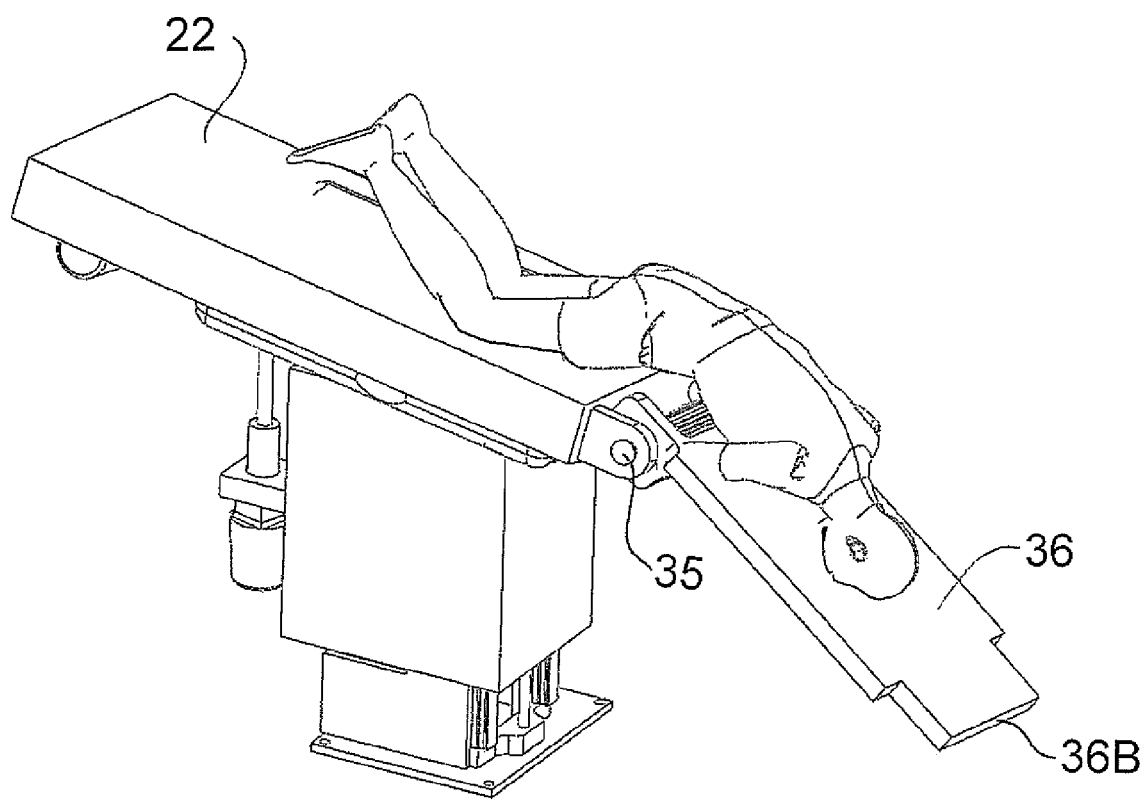
FIG. 5 is an isometric view of the table of FIG. 1 for mounting the patient showing a configuration for spine procedure.

The replaceable table top portion 24 in FIG. 2 includes a transverse hinge 35 which allows a cantilevered portion 36 of the table top portion to be moved upwardly and downwardly to take up different angles as indicated at 37 relative to the main table member 22. This forward portion 36 which is cantilevered beyond the hinge line can pivot upwardly and downwardly to positive and negative angles. As shown in FIG. 3, the portion 36 is pivoted upwardly relative to the table top member 22 so as to provide an angle less than 180°. In FIG. 5, the same table top portion 36 is pivoted downwardly relative to the table member 22.

Alternative arrangements (not shown) can be provided which provide a further transverse hinge line spaced outwardly from the hinge line 35 allowing further bending movement of the table top portion.

In use, the patient is placed upon the table top in a configuration arranged for surgery of the patient at the required location. Further details described hereinafter provide a number of examples of such configurations. However other configurations are also possible.

Thus the patient on the operating table is located in a position which is particularly suitable for operation by the surgeon on the part of the patient to be treated. The surgery does not need to be invasive and any form of intervention is possible using the table structure described. In addition the table structure can be used for radiation treatment where the patient is located in a suitable configuration for the radiation to be applied to the required location.

With the patient arranged for the surgery or other intervention, the patient while remaining in that configuration and while held in that configuration by suitable restraints, can be moved into the bore of the magnet typically by movement of the magnet longitudinally along its length in accordance with the Hoult patent set forth above. Thus the cylindrical bore of the magnet is moved over the table and over the patient on the table with the table adjusted to a position which will allow the magnet to pass over the table and the patient. Thus prior to movement of the magnet, while the patient remains in the configuration required for surgery, the table may be adjusted in height for an angle in accordance with any of the above allowable movements to position the table so that the magnet bore can move over the patient and the table.

In addition, with the magnet in place, the part of the patient is located generally at the field of view within the magnet for imaging.

However the configuration of the patient on the table and the position of the table allowing the movement of the magnet to the required imaging position likely will not position the part of the patient at the best location within the field of view to obtain the desirable imaging parameters.

Thus while the patient and the table are within the bore, the table is adjustable so as to move the part of the patient to the best position for imaging. This movement can be calculated, bearing in mind all of the available potential movements which can be made so as to best position the patient while avoiding significant movement of the patient out of the configuration set for the surgical procedure. In some cases some adjustment for the configuration is necessary in this movement within the bore but it will be appreciated that this is minimized in order to avoid compromising the surgical procedure. In some cases no movement of the configuration is possible in which case the movements allowed of the table are limited to those movements which maintain the configuration unchanged while optimizing the position of the part of the patient for imaging.

A system is provided to prevent damaging collisions between the patient and the table on one hand and the magnet on the other hand.

Control systems can be provided which calculate the position of the table and the patient prior to entry into the bore and during movement of the patient within the bore so as to avoid moving the patient to a position in which impact with the bore of the magnet may occur.

However for effective safety procedures it is also necessary to provide an impact detection system between the patient and the bore.

In one example this is provided using a laser system positioned within the bore which provides a series of beams within the bore which are broken in the event that the table or the patient approaches to close to the bore of the magnet. Such beams include directional arrangements together with receptors which receive the beams in their unbroken position and provide an indication if anyone of the beams is broken due to the movement of the patient or the table.

In a second example, an arrangement is provided which detects actual contact between an object and the inside surface of the bore. This construction may be of the type shown in U.S. Pat. No. 7,446,304 (Li) issued Nov. 4, 2008 to the present assignees, the disclosure of which is incorporated herein by reference. In this arrangement, therefore, the inside surface of the bore carries a flexible receiving surface which is deflected in the event of contact with an object within the bore so that the further movement of the patient and the table can be halted as soon as such a deflection is determined.

As a further alternative, a deflection system of this type can be provided on the table and/or on elements surrounding and identifying the location of the patient. Thus impact of the bore on the table itself or on one of these elements identifying the position of the patient triggers a signal in the element itself which again halts the movement of the patient and the table to the unsuitable position.

Turning now to FIG. 3, there is shown an arrangement of the table which is established for procedures on the head of the patient. In this arrangement the patient is positioned on the table so that the legs of the patient are on the table member 22 with the knees of the patient at the hinge line 35. The portion 36 is then inclined upwardly and forwardly from the hinge line 35 so that the portion 22 and the portion 36 define a shallow obtuse angle. As shown the table portion 22 is inclined forwardly and downwardly. In this arrangement the table portion 36 includes a head mount 40 with a clamp 41 and a mounting bracket 42. The mounting bracket 42 is attached on the underside of the end of the portion 36 at a narrower section 36A. The bracket is located underneath the forward end of the portion 36 so that the clamp 41 is positioned forwardly and downwardly from the end 36B of the portion 36. In this way the patient is laid prone on the table with the head facing downwardly and forwardly thus exposing the rear 43 of the head 44 for suitable surgical procedure at the rear of the skull or the base of the skull.

The positioning of the head of the patient forwardly and downwardly allows the configuration of the patient to be suitably arranged so that the patient can enter the bore. Once within the bore, the position of the head of the patient can be adjusted forwardly, rearwardly, side to side together with up and down and tilt movement as previously described so as to position the part of the head to be imaged in the best position within the field of view within the magnet.

Figure 4:
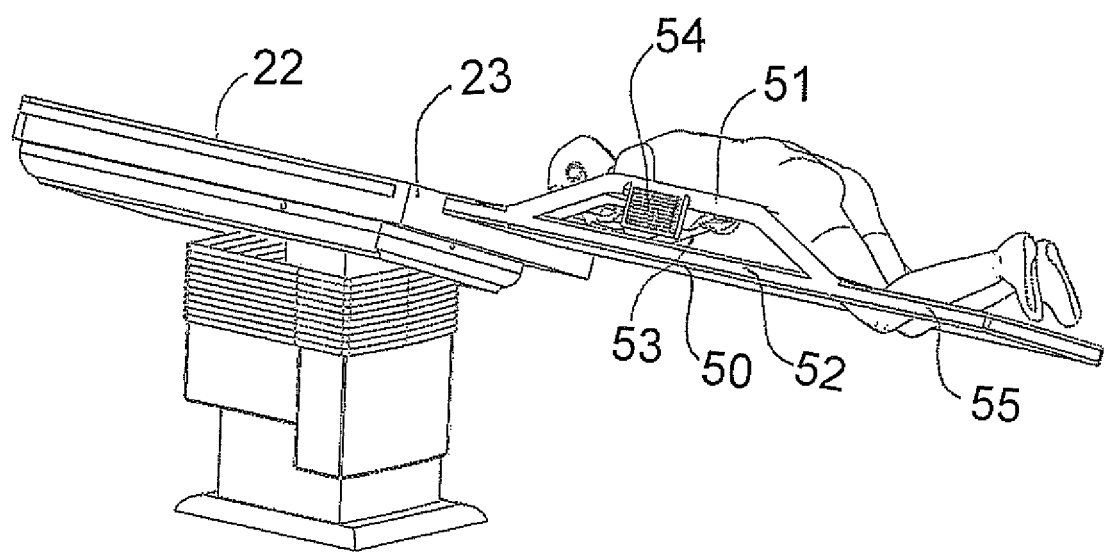
FIG. 4 is an isometric view of the table of FIG. 1 for mounting the patient showing a configuration for breast procedure.

In FIG. 4 is shown a construction provided for operations on the breast. In this arrangement, the table member 22 as a replacement table portion 50 attached at the receptacle 23. The table portion 50 has no transverse hinge line and is formed from a frame structure providing an arch section 51 over the base planar portion 52. The arch portion 51 has two sides located on respective sides of the patient together with transverse members which support the patient when laid in prone condition over the arch section 51 so that the breast area of the patient is located underneath the arch and above the planar base position 50 to allow access from open sides 53 of the structure. The arched frame 51 providing the openings 53 also allows for mounting of the RF coils 54. In this way the patient is supported prone with the knees projecting downwardly and rearwardly from the rear of the arch with a patient draped over the arch and the knees and feet carried on the planar portion 50 at an outwardly projecting section 55 of that planar portion. Again the position of the patient within the bore after insertion of the patient into the bore can be adjusted by tilting movement as required to move the part to be imaged to the required position. The patient remains in the configuration draped over the arch and can be held in that position by straps or other restraints allowing the table to be tilted to one side if required for proper positioning of the part to be imaged.

For breast procedures, the patient is positioned face down (prone) with an opening on the breast area. Cushions support the head and the rest of the body through the sternum with the legs and upper pelvic are being bent. The position allows full unilateral and bilateral access to the breasts.

The arrangement of FIG. 5 can also utilize the known Wilson frame available from OSI of Union City Calif., the details of which are known to persons skilled in the art.

Turning now to FIG. 5, there is shown the structure used in FIGS. 2 and 3 in which the same structure is used for operation typically on the spine or back of the patient. In this arrangement, therefore, the hinge line 35 is located around the waist area of the patient with the legs located on the table member 22 and the upper torso of the patient draped in prone condition over the portion 36. In this arrangement the head is positioned at a location spaced from the forward most end of the portion 36. The portion 36 is bent downwardly so as to provide an angle slightly greater than the 180° so that the back area of the patient is stretched over the hinge line 35 allowing effective access to the back and spine of the patient. Again the arrangement as shown allows the structure to be properly positioned with the patient remaining the configuration required into the bore and then for the movement of the table to adjust the patient to the required position for imaging without changing the configuration of the patient that has been set for the surgery.

Figure 6:
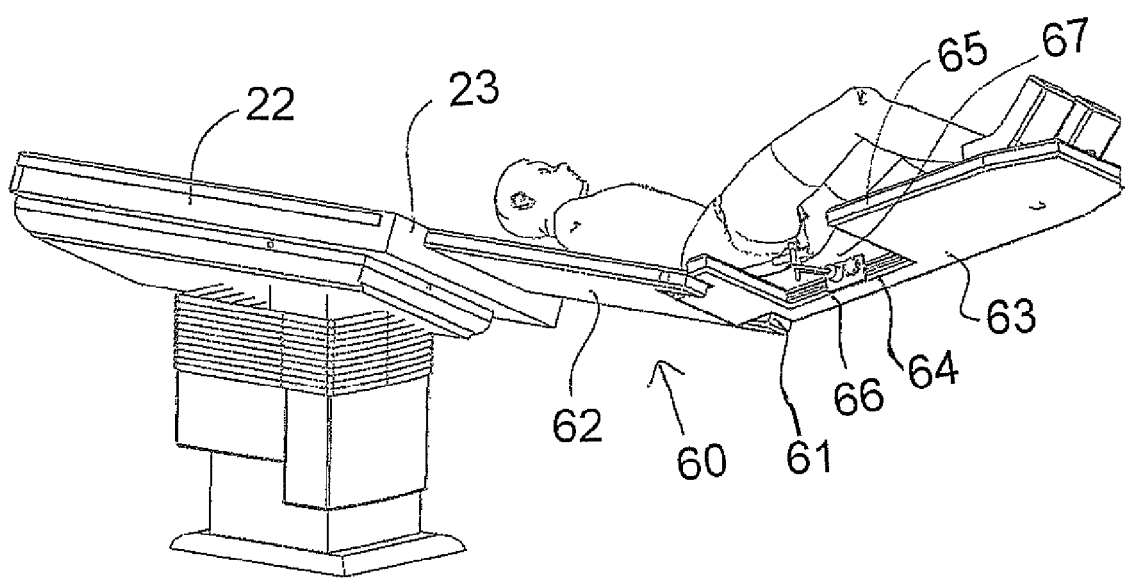
FIG. 6 is an isometric view of the table of FIG. 1 for mounting the patient showing a configuration for groin procedure.

Turning now to FIG. 6, there is shown a further arrangement of the table which utilizes a further table top portion 60 mounted on the table member 22 at the receptacle 23. In this arrangement the table top portion is designed for operation in the groin area for various procedures which are necessary at that location of the body. In this arrangement there is provided a hinge line 61 which is located at a position spaced from the table member 22 so as to provide a first portion 62 and a second portion 63 which can be arranged at an angle at the hinge line 61. An opening 64 is located in the second portion 63 just beyond the hinge line and extends from one side 65 to a narrow section 66 on the opposite side of the portion 63. This provides an opening 67 through which access can be made to the patient in the area required.

The invention claimed is:

1. A method for imaging of a part of a patient using Magnetic Resonance prior to or at one or more intermediate times during a surgical procedure, the method comprising:

using an MRI system including a magnet arrangement having a field of view and a patient support table for supporting a patient;

outside the magnet, placing the patient on the table in a configuration arranged for the surgical procedure;

while the patient remains substantially stationary in the configuration on the table, causing movement of either the table or the magnet so that the patient is moved into the field of view of the magnet;

while the patient remains substantially stationary in the configuration on the table and while the patient is in the field of view, causing movement of the table relative to the magnet so as to adjust the position of the patient relative to the field of view so as to locate the position of the part of the patient to be imaged more effectively within the field of view of the magnet;

while the patient remains substantially stationary in the configuration on the table, causing movement of either the table or the magnet so that the patient is removed from the magnet for the surgical procedure.

2. The method according to claim 1 including causing imaging of the MRI system while the table and the magnet remain stationary.

3. The method according to claim 1 wherein the position of the patient in the bore is adjusted to optimize the position of the part to be imaged in the field of view.

4. The method according to claim 1 wherein there is provided a control system which includes an input for entering into a memory a set position of the table and wherein the control system is arranged to return the position of the table to the set position when instructed to do so.

5. The method according to claim 1 wherein the table is continuously articulated inside the bore during imaging.

6. The method according to claim 1 wherein the patient support table is arranged for movements which include at least:

longitudinal movement along the longitudinal axis of the table;

transverse movement side to side;

rolling movement about a longitudinal axis of the table;
tilting movement about a transverse axis of the table;
a bending movement of the table relative to a transverse hinge line in the table at a position spaced from the ends of the table.

7. The method according to claim 6 wherein the bending movement of the table is both upward and downward of a planar central position of the table.

8. The method according to claim 6 wherein the movements include bending movements of the table relative to two or more transverse hinge lines in the table.

9. The method according to claim 6 wherein the table is arranged to receive the patient lying on the table and wherein the table includes a first transverse hinge line in the table is at one end of the table at one end of the patient and a second transverse hinge line at a position part way along the patient.

10. The method according to claim 1 wherein the table comprises a planar board with a flat top surface and a flat bottom surface generally parallel to the top surface with a vertical thickness between the surfaces of less than 2.0 inches.

11. The method according to claim 1 wherein the table has pedestal and a table top with the table top cantilevered by a length such that the whole of the patient is carried on the cantilevered portion.

12. The method according to claim 1 wherein the table has a pedestal which is on wheels for movement of the table.

13. The method according to claim 12 wherein the movement can be locked.

14. The method according to claim 1 wherein there is provided an impact detection system for detecting impact of the patient or the table with an interior surface of the bore of the magnet.

15. The method according to claim 14 wherein the impact detection system operates by providing a laser transmitter generating a beam and a receiver for the beam and where breaking of the beam is indicative of a potential impact.

16. The method according to claim 14 wherein the impact detection system operates by providing a contact sensitive sensing system on the interior surface of the magnet.

17. The method according to claim 1 wherein the movement is effected by motors which are MR compatible and at least some of which are in the bore during the movement.

18. The method according to claim 1 wherein in one of the configurations the patient is prone and the table is arranged to tilt the head downwardly and forwardly.

19. The method according to claim 18 wherein the table provides a hinge line across the hips of patient allowing a forward part of the table with the upper body of the patient thereon to tilt downwardly and forwardly.

20. The method according to claim 1 wherein the table includes a head holder which allows the head of the patient to tilt downwardly from the end of the table and the table includes a hinge portion which tilts upwardly and forwardly with the head holder beyond the end of the hinge portion.

21. The method according to claim 1 wherein in one of the configurations the patient is arranged for surgery in the groin area and wherein the table is arranged with a first portion on which the upper body part is received, a hinge line in the area of the hips and a second part to receive the lower body part hinged at the hinge line relative to the first part and wherein the second part includes an opening through which the groin area can be accessed.

22. The method according to claim 1 wherein in one of the configurations the patient is arranged for surgery of the breast and wherein the table is arranged with an arched portion onto which the patient is placed in prone position, the arched portion having an opening from the sides through which the breast can be accessed.

23. Apparatus for use in imaging of a part of a patient using Magnetic Resonance comprising:
a magnet arrangement having a field of view;
a patient support table for supporting a patient;
a control system for controlling relative movement of the table and the magnet;
the patient support table being arranged for movements which include at least:
longitudinal movement along the longitudinal axis of the table;
transverse movement side to side;
rolling movement about a longitudinal axis of the table;
tilting movement about a transverse axis of the table;
a bending movement of the table relative to a transverse hinge line in the table at a position spaced from the ends of the table;
the control system being arranged to effect said movements while the patient support table is within the field of view.

* * * * *